United States Patent
Loeb et al.

(10) Patent No.: US 6,658,301 B2
(45) Date of Patent: Dec. 2, 2003

(54) METHOD AND APPARATUS FOR CONDITIONING MUSCLES DURING SLEEP

(75) Inventors: Gerald E. Loeb, South Pasadena, CA (US); Frances J. R. Richmond, South Pasadena, CA (US)

(73) Assignee: Alfred E. Mann Institute for Biomedical Engineering at the University of Southern California, Los Angeles, CA (US)

(*) Notice: Subject to any disclaimer, the term of this patent is extended or adjusted under 35 U.S.C. 154(b) by 0 days.

(21) Appl. No.: 09/952,950

(22) Filed: Sep. 13, 2001

(65) Prior Publication Data

US 2003/0093131 A1 May 15, 2003

Related U.S. Application Data

(60) Provisional application No. 60/232,131, filed on Sep. 13, 2000.

(51) Int. Cl.⁷ .................................................. A61N 1/40
(52) U.S. Cl. ........................................... 607/65; 607/61
(58) Field of Search ............................... 607/2, 46–156

(56) References Cited

U.S. PATENT DOCUMENTS

| | | |
|---|---|---|
| 5,193,539 A | 3/1993 | Schulman et al. |
| 5,193,540 A | 3/1993 | Schulman et al. |
| 5,312,439 A | 5/1994 | Loeb et al. |
| 5,324,316 A | 6/1994 | Schulman et al. |
| 5,405,367 A | 4/1995 | Schulman et al. |
| 5,697,076 A | 12/1997 | Troyk et al. |
| 6,051,017 A | 4/2000 | Loeb et al. |
| 6,061,596 A | 5/2000 | Richmond et al. |
| 6,164,284 A | 12/2000 | Schulman et al. |
| 6,185,452 B1 | 2/2001 | Schulman et al. |
| 6,185,455 B1 | 2/2001 | Loeb et al. |
| 6,208,894 B1 | 3/2001 | Schulman et al. |
| 6,240,316 B1 | 5/2001 | Richmond et al. |
| 6,315,721 B2 | 11/2001 | Schulman et al. |
| 6,366,817 B1 * | 4/2002 | Kung |

* cited by examiner

Primary Examiner—Scott M. Getzow
(74) Attorney, Agent, or Firm—McDermott, Will & Emery

(57) ABSTRACT

A method and apparatus for conditioning muscles during sleep. The apparatus includes microminiature electrical stimulators that are injected into the muscles to be exercised and a system of transmission coils located in or on the mattress of a bed. The transmission coils transmit power and command signals to the implanted electrical stimulators while the patient sleeps or rests. The implanted electrical stimulators can be programmed so as to produce the desired pattern of muscle exercise without producing cutaneous sensations that would disturb the patient.

16 Claims, 2 Drawing Sheets

METHOD AND APPARATUS FOR CONDITIONING MUSCLES DURING SLEEP

RELATED APPLICATIONS

This application claims the filing date benefit of U.S. Provisional Application No. 60/232,131, filed on Sep. 13, 2000, entitled "Method and Apparatus for Conditioning Muscles During Sleep", the contents of which are incorporated herein.

BACKGROUND OF THE INVENTION

1. Field of the Invention

This invention relates generally to medical systems for the treatment of atrophied or spastic muscles. More particularly, the present invention relates to a system and method for electrically stimulating muscles during sleep.

2. General Background and State of the Art

There are many medical conditions for which it is desirable but difficult or impossible to exercise particular muscles to build their strength or reduce spasticity. Medical conditions such as stroke, spinal cord injury and cerebral palsy result in paralyzed, weakened and/or spastic muscles as a result of deficits of descending control from the brain to the spinal cord. Weakness, atrophy and imbalances of muscle function occur also as secondary problems of joint pathology such as arthritis in which pain inhibits normal muscle use. Electrical stimulation can be used to strengthen such muscles, preventing disuse atrophy and correcting spasticity and contractures that result from imbalances in antagonistic pairs of muscles. Electrical stimulation excites the peripheral axons of motoneurons, which in turn activate the muscle fibers that they innervate via synaptic connections. The resulting activation of muscle fibers exerts effects similar to normal voluntary exercise, improving the strength and fatigue resistance of the stimulated muscles and stretching spastic antagonist muscles, preventing contractures. These useful effects of exercise are well recognized by sport coaches, athletic trainers, physical therapists and practitioners of sports medicine and exercise physiology, although the trophic physiological mechanisms underlying such effects are not well understood.

Electrical stimulation tends to excite any large diameter sensory axons that happen to be in the vicinity, as well as the motor axons that are the usual target of therapeutic electrical stimulation. When the stimulating current is applied via electrodes within the muscle or on a muscle nerve, the nearby large diameter sensory axons arise mostly from proprioceptors. The reflex effect of such proprioceptive activation tends to excite further the motoneurons controlling the stimulated muscle and its synergists. Other reflex effects of such proprioceptive activation tend often to inhibit the activity of motoneurons controlling antagonist muscles. Both of these are useful effects, both acutely to enhance the effects of the motor stimulation and chronically to reduce hyper-reflexive spasticity. In contrast, when the stimulating current is applied through the skin or onto mixed peripheral nerve trunks containing both muscular and cutaneous components, the large diameter axons that are activated will include the mechanoreceptors of the skin. Such activation produces a variety of reflex actions, often inhibiting voluntary muscle function. It also gives rise to various conscious sensations that may be distracting or unpleasant depending on the site, strength and duration of the stimulation.

Some devices comprising microstimulator implants themselves and for certain applications including therapeutic electrical stimulation (TES) have been developed. This application contains reference to U.S. Pat. Nos. 6,051,017, 6,061,596, 5,312,439, 5,405,367, 5,193,539, 5,193,540, and 5,324,316 which describe microstimulator implants, each of which is hereby incorporated by reference in their entirety.

U.S. Pat. No. 6,240,316 describes the use of microstimulators for the treatment of sleep apnea in which the transmission coil is located under the sleeping patient, but this is a form of neuromodulatory stimulation rather than therapeutic stimulation. In neuromodulatory stimulation (NMS), the stimulation pulses themselves are used to create a desired physiological response; a common example is a cardiac pacemaker. In TES, the stimulation pulses are used to exercise the muscles and neural pathways so as to induce long-term changes in their structure and function according to trophic principles whereby various body tissues adjust their properties in response to the demands of regular usage patterns. This invention is particularly applicable to TES applications, which generally require fairly intense stimulation over substantial periods of time, often delivered to multiple sites.

The sleep apnea patent describes the use of a single transmission coil, which is easily located in a collar or pillow that moves with the patient during sleep. The switched transmitter coil technology described in this application is particularly important when stimulating limb or trunk muscles, particularly in children who tend to move a lot during their sleep, but it may also be useful for the sleep apnea application. The sleep apnea application was presented in two forms: one with back-telemetry of signals from a sensor of respiratory movement and one with stimulation only and no back-telemetry, which substantially simplifies the system. This invention requires that back-telemetry be available to track the position and responses of the implanted stimulators but it does not require a separate sensing function.

Other relevant technology can be found in the area of transcutaneous electrical nerve stimulators (TENS) and percutaneous wire electrodes injected into muscles and used for functional electrical stimulation (FES). An implanted system for FES of the arm called FreeHand™ has been marketed by NeuroControl Corp. of Cleveland, Ohio. It is controlled by an inductive RF link similar to a cochlear implant, with an external transmission coil designed for close coupling; it is not intended or suitable for use while sleeping. A stimulator for strengthening shoulder muscles that employs fine wires inserted into the target muscles and passing physically through the skin for connection to a more conventional electrical stimulator is presently being tested by the same company. Such a system would be possible, albeit awkward, to use during sleep, but its vulnerable percutaneous leads make it unsuitable for long-term use. Transcutaneous stimulation (electrodes attached adhesively to the surface of the skin) has been used to condition muscles in patients at rest, but the high stimulus strength required to activate deep muscles invariably produces strong cutaneous sensations which are usually unpleasant and likely to interfere with sleep.

In order to obtain useful therapeutic results in muscles, it can be necessary to apply electrical stimulation for several hours per day over many months. Thus it is important to minimize the disruptive effects of the therapy, particularly for younger and older patients who may be reluctant to comply with such prescribed treatment. Disruptive effects include the time and attention required to set up stimulation equipment, time taken from other activities of daily living to receive the treatment, and any unpleasant sensations associated with the electrical stimulation. It is also important to minimize the overall cost of chronic treatment and to minimize possible medical complications such as damage to skin and muscles, as well as wound infections and morbidity that may arise from surgical procedures.

Therapeutic electrical stimulation (TES) of muscles is most commonly applied by the transcutaneous approach, in which electrodes are affixed to the skin overlying the so-called motor point of the muscles to be electrically exercised. This is the region where the muscle nerve enters the muscle, in theory permitting relatively selective and complete activation of the muscle. In reality, quite high voltages and currents are required to activate motor axons that pass deep to the skin surface, resulting in substantial activation of more superficial cutaneous nerves. Even when accurately positioned by an experienced therapist, such electrodes often fail to activate completely the target muscles, particularly if they are located deep to the skin surface. At each treatment session, stimulation levels must be adjusted carefully to maximize the desired therapeutic effects and minimize unpleasant sensations. The therapist must watch for skin irritation that may be produced by the stimulation, particularly if the electrodes are affixed poorly or become dislodged during use. For these reasons, TES is used only infrequently despite its potentially beneficial effects, and is generally deemed to be impractical for young patients with cerebral palsy and older patients with strokes for whom it would be particularly useful.

A less common approach to TES is percutaneous, intramuscular wire electrodes. Fine wires are injected into the target muscles through a hypodermic needle and remain chronically in place with their leads extending through the skin. When treatment is applied, the external ends of the leads are attached to a conventional electrical stimulator. This intramuscular approach provides selective stimulation of the motor neurons innervating the target muscle without exciting other muscle or skin nerves. The required stimulation currents tend to remain constant as long as the electrode tips are not dislodged from the muscle. The percutaneous wires pose significant dangers of infection and dislodgment, however, and are not suitable for long term use in most patients, particularly those already disabled by their underlying neurological problems.

Other approaches to electrical stimulation of muscle are known but are not generally suitable for chronic TES. Magnetic stimulation can induce electrical currents sufficient to activate motor axons, but this is even less selective and more difficult to apply than transcutaneous stimulation. Fully implanted stimulators similar to cardiac pacemakers have been used for functional electrical stimulation to reanimate paralyzed limbs, but the devices are expensive and they require extensive surgery to implant and route their leads to various target muscles.

SUMMARY OF THE INVENTION

Accordingly, an object of the present invention is to provide a method and apparatus for applying therapeutic electrical stimulation (TES) to specific muscles while a patient sleeps. It is a further object to permit patients themselves and/or their domestic caregivers to administer TES in an easy to use manner without requiring trained assistance for each treatment session.

The present invention teaches the application of electrical stimulation to activate such muscles via means suitable for use during sleep. The apparatus includes microminiature electrical stimulators that are injected into the muscles to be exercised and a system of transmission coils located in or on the mattress of a bed. The transmission coils transmit power and command signals to the implanted electrical stimulators while the patient sleeps or rests. The implanted electrical stimulators can be programmed so as to produce the desired pattern of muscle exercise without producing cutaneous sensations that would disturb the patient.

The invention includes two primary features. First is an intramuscular microstimulator (called a BION™), one or more of which are injected into the muscles to be exercised, where they generate stimulation pulses upon commands transmitted to them from an external controller. Additionally there is an external controller (called Personal Trainer™), which transmits power and command signals to the BIONs by means of one or more inductive coils placed in or on a mattress while the patient sleeps.

In one embodiment of the invention, the BIONs verify that they have received a given command signal by emitting a confirmatory signal that is detected via the inductive coil that transmitted the command. In the absence of such a confirmation, the Personal Trainer can switch the command signal to another transmission coil in order to accommodate motion of the patient during sleep.

The invention further includes a system for exercising muscles while a patient sleeps, comprising a microstimulator implanted into the body, an inductive coil placed in or on a surface upon which the patient rests, and a controller capable of transmitting power and commands to the microstimulator via one or more inductive coils external to the body.

The invention also includes a system for exercising muscles while a patient sleeps comprising a microstimulator capable of emitting a signal in response to a command, where the signal is detectable by a controller.

The invention additionally includes a system for exercising muscles while a patient sleeps comprising a controller capable of switching among a multiplicity of inductive coils so as to find at least one or more inductive coils which can be used successfully to transmit commands to a given microstimulator.

DETAILED DESCRIPTION OF THE EXEMPLARY EMBODIMENTS

Figure 1B:
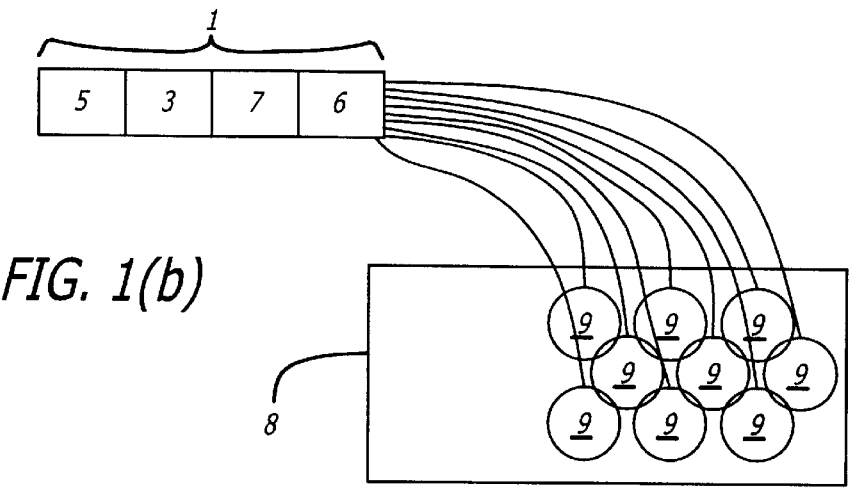
FIGS. 1A and 1B are schematics of exemplary embodiments of the system of the invention.
Figure 1A:
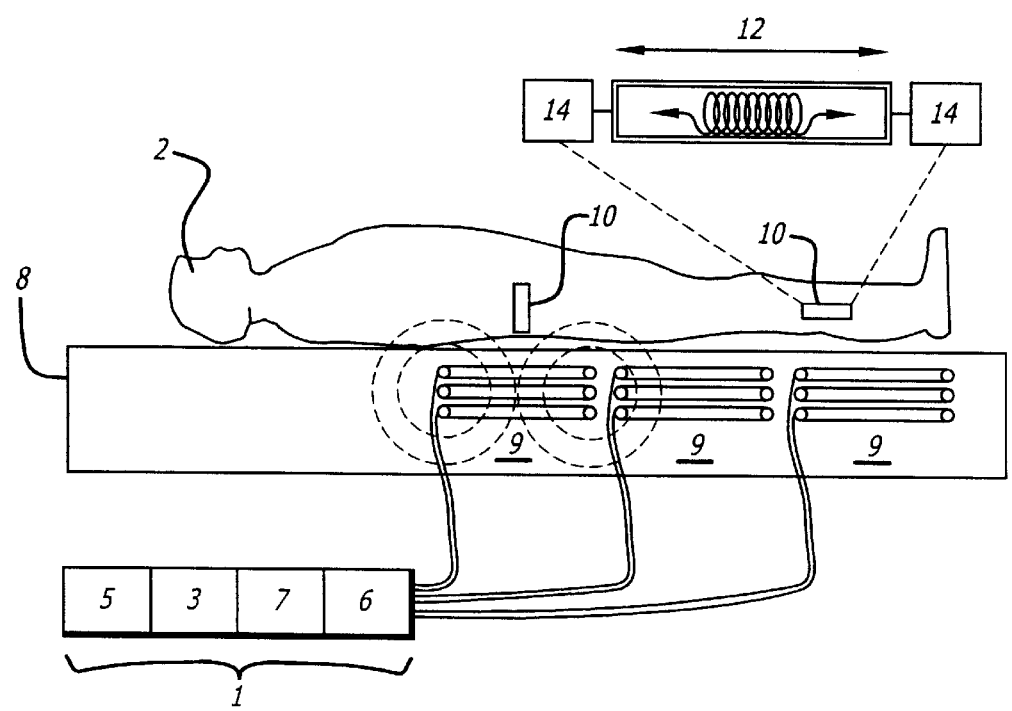

FIGS. 1A and 1B show a schematic of exemplary embodiments of the system of the invention, which are divided between an external component 1 and one or more implants 10 that are advantageously located in or near the nerve(s) or muscle(s) to be electrically stimulated within patient 2.

Implanted electronic devices 10 each consist of a hermetically sealed capsule 12 in which are located electronic circuitry and to which are attached a pair of electrodes 14. Said electronic circuitry will typically include an inductive coil, power storage capacitor, and integrated circuit for performing various functions as detailed below and illustrated schematically in FIG. 2. Upon command from the external component 1, an implanted electronic device 10 emits an electrical stimulation pulse that travels through the body tissues between and around its electrodes 14, thereby activating local nerve fibers as required. By selecting appropriately the strength and temporal patterning of such stimulation, the desired therapeutic effect can be achieved.

External electronic means 1 transmits power and command signals to implanted electronic devices 10 by creating a modulated radio frequency (RF) field on one of several inductive coils 9 disposed at various locations in or on the sleeping surface 8. Advantageously, said inductive coils 9 can be disposed in an overlapping pattern as depicted in FIG. 1b (Top view) so that both vertically and horizontally oriented magnetic fields can be generated over any portion of the sleeping surface 8. This is useful because during sleep the implanted electronic devices 10 may shift in both location and orientation (i.e. lying predominantly vertical or horizontal) with respect to sleeping surface 8, as depicted in FIG. 1a (side view). The magnetic field is more effective at energizing a given implant when it is aligned more or less parallel with the long axis of the inductive coil contained within said implant.

Advantageously, in an exemplary embodiment of the present invention, the modulated radio frequency magnetic field required to energize and control the implanted electronic devices 10 is created by Driver circuitry 7 employing a variant of Class E power oscillator called "suspended carrier transmission", described more fully in U.S. Pat. Nos. 5,179,511 and 5,697,076, which are incorporated herein by reference. In this scheme, depicted here in FIG. 2, a very high Q resonant circuit (Q>100) consisting of inductive coil 9 and a tuning capacitor can be energized to a high level of inductive field strength while drawing only a small current from a power supply. When the peak sustained oscillations have been achieved in inductive coil 9, the carrier can be 100% modulated by opening a switch 6 in the circuit between the tuning capacitor and the coil at precisely the instant when the current through the coil is zero and the voltage on the capacitor is maximal. The carrier can be reinstated rapidly and with minimal energy loss by closing the switch 6. The number of cycles in which the carrier is on or off can be used to encode digital data for the purpose of controlling implanted electronic devices 10. When the switch 6 is open and the carrier is off, inductive coil 9 can be used as a high impedance antenna to detect outgoing emissions that encode information from implanted electronic devices 10. Other systems for encoding data onto RF transmissions are known in the art and could be employed alternatively within the scope of the invention claimed herein. These include frequency shift keying, phase shift keying, and reflected subcarriers, among others that would be obvious to one skilled in the art. A "modulated reactance" circuit for producing various types of modulation in a very high Q class E oscillator has been described by G. E. Loeb, R. A. Peck, W. H. Moore and K. Hood in Medical Engineering and Physics, vol. 23, pp. 9–18, January, 2001 ("BION system for distributed neural prosthetic interfaces"), and is incorporated herein by reference.

Figure 2:
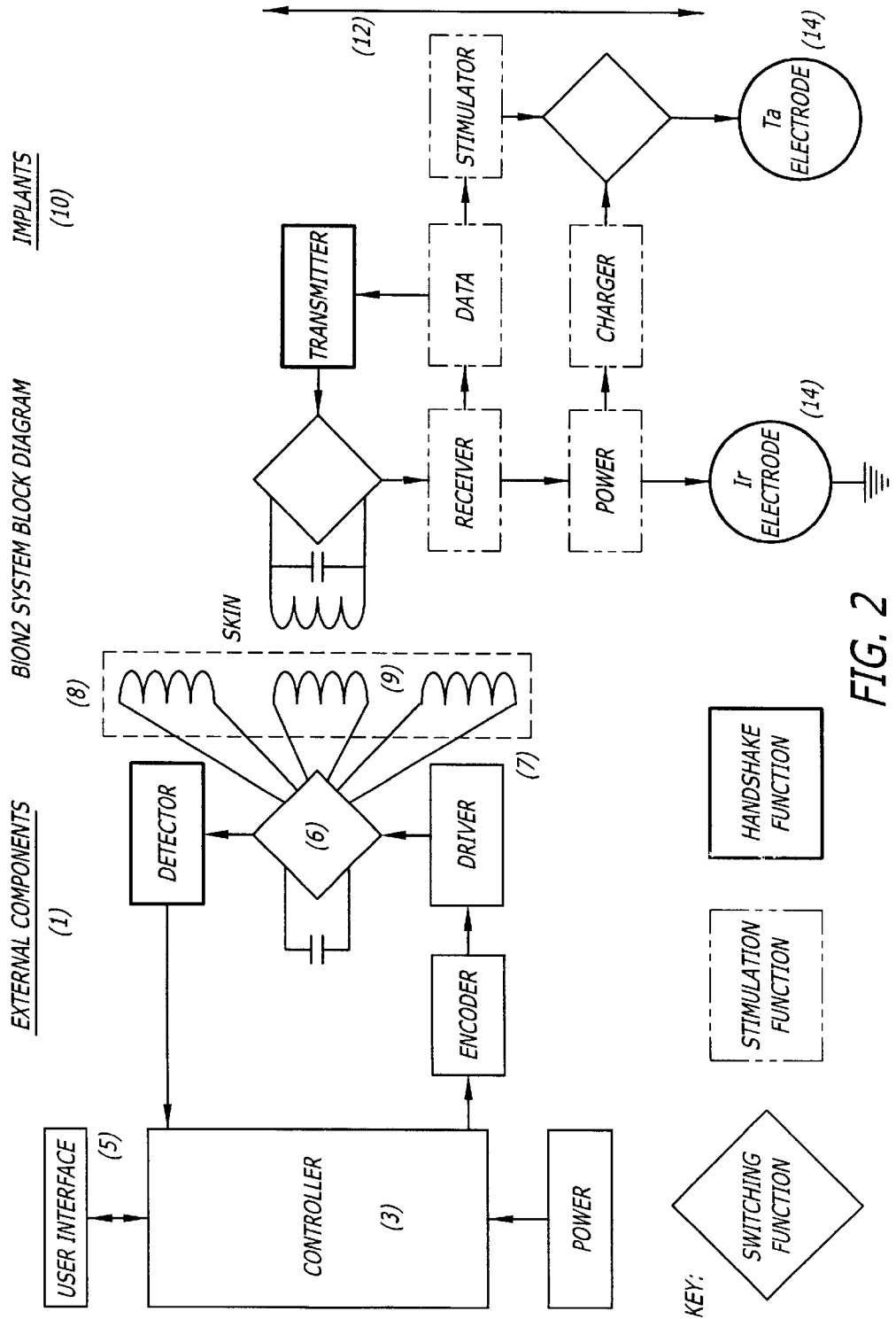
FIG. 2 is a block schematic of the electronic functions performed by circuitry within the external and implanted components of the present invention.

In the preferred embodiment depicted in FIG. 2, switching function 6 selects one of the available inductive coils 9 for energizing. By switching sequentially to energize each inductive coil 9, it is likely that at least one command will successfully reach each implant 10. Thus, switching function 6 is a multipolar electronic version of the switch 6 required by suspended carrier modulation as taught by Troyk et al. in U.S. Pat. No. 5,697,076. Because the modulation switch 6 opens and closes synchronously with the zero crossing of current through the inductive coil being energized, such a multipolar switch can be used to shift the connection to another one of such inductive coils 9 rapidly and with minimal power dissipation or waveform distortion.

When an implant is located sufficiently close to a transmission coil 9 that is active, it receives sufficient electrical energy by inductive coupling to the magnetic field created by said active transmission coil 9, enabling said implant to energize its electronic circuitry and decode the command signals carried by the modulations of that magnetic field. The first few bits of data contain an address that specifies which of several implants 10 is to deliver a stimulation pulse. If the transmitted address matches the address that is represented electronically in the implant, then the implant decodes the remaining data bits, which specify the strength and duration of the stimulation pulse to be delivered. During or at the end of the data transmission, one or more parity bits are used to assure the integrity of the received data. If the data transmission is correct, the implant generates the requested stimulation pulse.

In an exemplary embodiment of the present invention, an implant 10 that has successfully generated a stimulation pulse then immediately transmits an outward-going pulse of RF energy. This outward telemetry signal is received and detected by the external component 1 as a "handshake" confirmation that the implant received and was able to respond to the request for a stimulation pulse. If no such confirmation is received, then control circuits in the external component 1 change the setting of switch 6 to another inductive coil 9 for transmission of power and data to the desired implant 10, continuing the switching and testing process until a handshake response is received. Controller 3 can maintain a record of which inductive coil was most recently successful in controlling each implant. Because the movements of the sleeping patient are relatively slow and infrequent, this permits controller 3 to minimize the time and power consumed in sending commands that are not received.

FIG. 2 provides an additional block diagram of the electronic functions performed by circuitry within the external and implanted components in order to support the operations described above. Referring to FIG. 2, the external components 1 may be subdivided into functional blocks. User Interface 5 provides control means whereby the user can instruct the system to begin or terminate TES and display means whereby the user can see or hear the state of the system, such as whether each implant 10 can be successfully powered and controlled from at least one inductive coil 9.

Controller 3 includes all digital circuitry required to operate the remainder of the system, including storage means that are loaded with and retain information specific to the patient and the implanted components, such as stimulus parameters required for the desired TES.

Power can be provided by AC/DC converter, batteries, or any suitable means.

Communication with the implanted devices is achieved by inductive coupling between one of the external inductive coils 9 and the inductive coil contained within each implant.

Driver 7 uses Class E circuitry to create a sufficiently high field strength of the RF carrier signal produced in external inductive coil 9 so that the voltage generated in each implant's inductive coil is sufficient to power the electronic circuitry in that implant. A tuning capacitor plus the external inductive coil 9 form a resonantly tuned tank circuit with a high Q.

An Encoder formats the digital command information from the controller 3 to each implant so that it can be applied to driver 7 in order to modulate the RF carrier signal so as to convey that command information to the implants.

After commanding an implant to generate a stimulation pulse, controller 3 must stop the transmission of RF power from external inductive coil 9 by opening an electronic switch 6 in the tank circuit at approximately the phase in the RF oscillation when the field strength in inductive coil 9 passes through zero. This causes inductive coil 9 to act like a high impedance antenna for the much weaker RF oscillations produced by the implant that is sending out the "handshake" signal confirming the delivery of the stimulation pulse.

A detector circuit amplifies and conditions the outgoing RF signal as picked up by inductive coil 9 acting as an antenna.

If no "handshake" signal is received, then controller 3 sets switch 6 to connect the driver 7 to another of the inductive coils 9, continuing in this manner until such a "handshake" is received. If none of the inductive coils 9 is capable of activating a given implant 9, then the appropriate preprogrammed action is taken by controller 3. This might include alerting the patient or a caregiver via User Interface 5 or recording the period of time when the prescribed TES could not be delivered and compensating with additional stimulation at a later time when the patient shifts position so as permit said implant to be controlled.

Referring to FIG. 2, the implanted devices 10 may each be subdivided in functional blocks.

The implant electronic circuitry 12 is contained within the hermetic package that protects it from moisture. It is connected a pair of electrodes 14 affixed outside the package so as to make electrical contact with the body tissues.

An inductive coil and capacitance that produces a resonant circuit tuned to the RF carrier frequency, wherein said capacitance includes self-capacitance of the coil windings plus any additional capacitance required for tuning.

In its idling state, the resonant circuit is connected to the Receiver circuitry, which extracts electrical power from the received RF carrier signal and directs it to a Power circuit and to a Data circuit. The Power circuit converts the RF power to a filtered and regulated DC voltage that powers the other circuitry. The Data circuit detects modulation of the RF carrier signal and converts these modulations to digital data that controls the operation of the remainder of the implant circuitry.

The received digital data addresses which implant 10 is to respond and specifies the strength and timing of an electrical pulse emitted through its electrodes 14, as controlled by the Stimulator function.

When a stimulation function is successfully initiated, the Transmitter function is activated simultaneously or shortly thereafter, causing an outgoing RF transmission of the same duration as the stimulation pulse to be generated using the tuned coil of the implant as a tank circuit and transmitting antenna.

When stimulation pulses are not being emitted but an RF carrier signal is being received, power extracted from said carrier is stored on the electrodes themselves by the Charger, as described by Loeb in U.S. Pat. No. 5,312,439 (May 17, 1994) and incorporated herein by reference. The Ta electrode is preanodized to approximately four times the maximal DC voltage produced by the Power and Charger circuitry so that it acts as an electrolytic storage capacitor with respect to the electrically conductive bodily fluids surrounding the electrode. This permits relatively large amounts of power to be stored and released in the form of intense, brief, intermittent stimulation pulses.

While the invention herein disclosed has been described by means of specific embodiments and applications thereof, numerous modifications and variations could be made thereto by those skilled in the art without departing from the scope of the invention as set forth in the claims.

We claim:

1. A method of exercising muscles during sleep, the method comprising the steps of:
    implanting at least one microstimulator so as to be in contact with muscular or nerve tissue; and
    externally generating power and command signals and transmitting it to the at least one microstimulator while a patient sleeps.

2. The method of claim 1 wherein the step of externally generating further comprises transmitting the power and signal commands through at least one inductive coil positioned inside or adjacent to the mattress on which a patient sleeps.

3. The method of claim 1 whereby the command signal is selected to generate a pattern of pulses so as to therapeutically condition muscles.

4. A method of exercising muscles during sleep, the method comprising the steps of:
    implanting at least one microstimulator so as to be in contact with muscular or nerve tissue;
    generating a command signal within an external transmitter;
    transmitting the command signal to at least one of a plurality of inductive coils;
    energizing at least one microstimulator upon alignment with the at least one inductive coil by further transmitting the command signal to the microstimulator;
    receiving the command signal at the microstimulator; and
    generating pulses at the microstimulator in response to the received command signal thereby activating local muscle and nerve tissues.

5. The method of claim 4 wherein the plurality of inductive coils are disposed within a sleeping surface in an overlapping pattern so that both vertically and horizontally oriented magnetic fields can be generated over any portion of the sleeping surface.

6. The method of claim 5 wherein the microstimulator further emits a signal in response to the commands and the signal is detected by a controller.

7. The method of claim 5 wherein a controller can switch the inductive coils to find at least one which can be used successfully to transmit commands to a given microstimulator.

8. The method of claim 5 wherein the inductive coils can be disposed in an overlapping pattern so that both vertically and horizontally oriented magnetic fields can be generated over different portions of the sleeping surface.

9. The method of claim 4 further comprising the step of emitting a response signal from the microstimulator to the external transmitter, acknowledging receipt of the command signal.

10. A method of exercising muscles during sleep, the method comprising the steps of:
    implanting at least one microstimulator so as to be in contact with muscular or nerve tissue;
    generating a command signal within an external transmitter;
    transmitting the command signal to at least one inductive coil;
    energizing at least one microstimulator upon alignment with the at least one inductive coil by further transmitting the command signal to the microstimulator;

receiving the command signal at the microstimulator; and generating pulses at the microstimulator in response to the received command signal thereby activating local muscle and nerve tissues.

11. A method of exercising a muscle within a body while the body is sleeping comprising:

generating an excitation signal;

delivering the excitation signal during sleep to a transmitting element that is external to the body;

receiving the excitation signal by a microstimulator implanted within the body and in electrical communication with the muscle or a nerve innervating the muscle; and delivering an exercising signal from the microstimulator to the muscle or nerve while the body is sleeping.

12. The method of claim 11 wherein the excitation signal includes a power signal.

13. The method of claim 11 wherein the excitation signal includes a command signal.

14. The method of claim 11 further comprising delivering a confirmation signal from the microstimulator back to the transmitting element.

15. A method of exercising a muscle within a body while the body is sleeping comprising:

transmitting a signal from a first of a plurality of transmission coils to a microstimulator implanted within the body and in electrical communication with the muscle or a nerve innervating the muscle;

detecting the absence of a confirming signal from the microstimulator to the first transmission coil;

transmitting a signal from a second of the plurality of transmission coils to the microstimulator;

detecting the presence of a confirming signal from the microstimulator to the second transmission coil; and delivering an exercising signal from the microstimulator to the muscle or nerve while the body is sleeping.

16. A system for exercising a muscle within a body while the body is sleeping comprising:

a plurality of transmission coils external to the body;

a controller connected to the transmission coils and configured in conjunction with the transmission coils to:

transmit a signal from a first of the transmission coils to a microstimulator implanted within the body and in electrical communication with the muscle or a nerve innervating the muscle;

detect the absence of a confirming signal from the microstimulator to the first transmission coil;

transmit a signal from a second of the transmission coils to the microstimulator;

detect the presence of a confirming signal from the microstimulator to the second transmission coil; and cause the microstimulator to deliver an exercising signal from the microstimulator to the muscle or nerve while the body is sleeping.

* * * * *